United States Patent [19]

Zupancic et al.

[11] Patent Number: 4,900,794
[45] Date of Patent: Feb. 13, 1990

[54] STYRENE TERMINATED MULTIFUNCTIONAL OLIGOMERIC PHENOLS AS NEW THERMOSETTING RESINS FOR COMPOSITES

[75] Inventors: Joseph J. Zupancic, Bensenville; Andrew M. Zweig, Schaumburg; James A. Wrezel, Buffalo Grove, all of Ill.

[73] Assignee: Allied-Signal Inc., Morris Township, Morris County, N.J.

[21] Appl. No.: 369,369

[22] Filed: Jun. 21, 1989

Related U.S. Application Data

[60] Division of Ser. No. 276,598, Nov. 28, 1988, Pat. No. 4,855,375, which is a continuation-in-part of Ser. No. 87,921, Aug. 21, 1987, abandoned.

[51] Int. Cl.$^4$ ................................................ C08F 8/00
[52] U.S. Cl. ............................... 525/326.3; 428/411.1; 522/135; 522/328.5; 522/328.6; 522/328.9
[58] Field of Search ............... 525/326.3, 328.5, 328.6, 525/328.9

Primary Examiner—Christopher Henderson
Attorney, Agent, or Firm—Harold N. Wells; Jay P. Friedenson

[57] ABSTRACT

Thermosetting resins which are essentially vinylbenzyl end-capped ethers of the oligomeric condensation products of certain dihydric phenols and formaldehyde are readily polymerized to give an extensively cross-linked polymer particularly useful in printed circuit boards and similar laminates. Effective cost reduction may be enjoyed by replacing up to 50% of the vinylbenzyl moieties by other groups, such as alkyl and benzyl groups, without destroying the usefulness of the resulting thermosetting resins. The vinylbenzyl ether product from bisphenol-A is especially recommended.

17 Claims, No Drawings

4,900,794

STYRENE TERMINATED MULTIFUNCTIONAL OLIGOMERIC PHENOLS AS NEW THERMOSETTING RESINS FOR COMPOSITES

CROSS REFERENCE TO RELATED APPLICATION

This application is a division of application Ser. No. 226,598, filed Nov. 28, 1988, now U.S. Pat. No. 4,855,375, application which is a continuation-in-part of our copending application, serial number 87,921, filed Aug. 21, 1987, now abandoned all of which is incorporated by reference.

BACKGROUND OF THE INVENTION

The subject matter of this application is directed toward resins used in the manufacture of reinforced plastics. More particularly, the resins (binders) are used in the preparation of composites formed from fibers embedded in a polymer resin matrix. Even more specifically this application is directed toward the use of such resins in the preparation of circuit board laminates where the reinforcing material is glass or quartz fiber.

To overcome some mechanical and structural limitations of plastics it has become relatively commonplace to reinforce them with other components. Composites formed of various fibers embedded in a polymer resin matrix are especially useful and susceptible to enormous variation depending upon the nature of the fiber used, how the fiber is utilized, and the matrix or binder for the fibers. Materials which have been used as fibers include glass, quartz, oriented polymers such as the aramids (Kevlar ™), graphite and boron. Whatever their composition such fibers can be used as chopped or continuous filaments, and when used as continuous filaments they can all be unidirectional or woven into a fabric. The matrix can be, for example, a polyester, epoxy, polyimide, polyetherketone or polyetherimide resin as either a thermoset or thermoplastic material. The uses for such composites range from airframes to tennis rackets and from boat hulls to rocket motor casings.

A particular area of composite application is that of printed circuit boards, especially multilayer circuit boards, for mounting electronic components. The use of glass fabric as the reinforcing material has become more-or-less standard and epoxy resins are most often used as the matrix. For the fiber to exert a reinforcing action it is necessary that the fibers be completely coated with resin, and to achieve this the glass fiber often is surface treated to provide sites for chemical bonding to the resin or to its precursor or for otherwise improved adhesion to the matrix material.

Multilayer circuit boards are laminates with alternating layers of composite and etched copper sheet. A brief discussion of their manufacture will aid in appreciating the properties requisite for such boards. A woven glass fabric is first impregnated with resin by dipping the cloth in a resin solution, often referred to as the varnish solution, in what is called the A-stage. Solvent is then removed to afford a glass cloth reinforced resin, or prepreg, in what is called the B-stage. In some cases the resin in the prepreg may be partially cured, in other cases uncured, but in all cases the prepreg is a non-tacky, readily handled rigid sheet of glass cloth embedded in and coated with a resin. The finished circuit board is prepared by laminting alternating layers of prepreg and etched copper foil under conditions of temperature and pressure where resin is cured, i.e., further polymerized and cross-linked to a final infusible, insoluble stage (C-stage).

From the above brief description some necessary and desirable characteristics of the resin may be readily discerned. The circuit board will be subjected to soldering temperatures and may be operated at an elevated temperature, or experience cyclic locally elevated temperatures because of local power generation, and thus the thermal coefficient of expansion of the resin should approximate that of glass to ensure continued dimensional stability and resistance to heat distortion. The resin should have a high solubility in the varnish solution to ensure high resin loading. The varnish solution should have a sufficiently low viscosity for even coating but not too low a viscosity as to run off the fibers. It is necessary that the prepreg not be tacky so that it can be readily handled and stored. The resin is desirably non-crystalline for enhanced solubility in the varnish solution and for good film forming properties in the prepreg. The resin should have adequate flow at the C-stage so as to make void-free laminated bonds, with the curing temperature somewhat higher than the glass transition temperature ($T_g$) of the resin to afford a wider processing "window." The resin also should be chemically resistant to a corrosive environment and to water vapor. To ensure that the discrete electrical components on a circuit board interact only via the etched path on the copper foil, it is desirable that the matrix have a low dielectric constant and high resistance.

The invention to be described is an amorphous, thermosetting resin which affords a varnish solution of high solids content with a viscosity leading to even coating without runoff, which affords a non-tacky prepreg, has a glass transition temperature sufficiently below the curing temperature to afford an adequate window of processing, and which shows excellent flow properties at the C-stage. The final cured resin exhibits a low dielectric constant and dissipation factor, a low coefficient of thermal expansion, and a high glass transition temperature. In short, we believe our cured resin has properties superior to those currently recognized as industry standards in the lamination of circuit boards, and thus presents outstanding benefits.

U.S. Pat. No. 4,116,936 describes thermosetting resins which are vinylbenzyl ethers of monomeric phenols, of simple phenol-formaldehyde condensation products commonly known as novolac resins, and of oligomers resulting from the reaction of a dihydric phenol, such as bisphenol A, and a glycidyl ether. However much these resins may represent an advance over prior art resins, presumably because the fully cured product shows, among other desirable properties, greater hydrolytic stability and corrosion resistance, we have discovered resins whose properties are decidedly superior in several operational aspects. In particular, whereas the resins of our invention show desirable flow at prepreg temperatures, they exhibit higher flow viscosity in solution at ambient temperature, thereby minimizing runoff and leading to improved coating uniformity. Additionally, the fully cured products of our resins show an improved coefficient of thermal expansion, a particularly important property in laminate production. Thermal expansion is a poorly understood function of the nature of the polymer backbone as well as the nature of the end capping group. The coefficient of thermal expansion can not be predicted, and obtaining thermosetting resins whose thermoset product has a coefficient of thermal expansion similar to that of, e.g., woven glass fabric remains a hit-or-miss affair. For our purposes an ideal fully cured product will have a coefficient of thermal expansion of about 30 ppm. The materials of our invention approach the goal closely.

The thermosetting resins of this invention do not appear to have a close analogue in the prior art, with the most relevant art of Wang et al., U.S. Pat. No. 4,707,558, only distantly related. The formulae of the patentees encompass a very large universe of permutations, and in the case where in their formula II $m'=0$ and $m=1$ one has a structure which is arguably, and only weakly arguably, pertinent to the materials of this invention. But even within such restrictions one requires a judicious choice of other of the patentees' variables, especially A and X, to arrive at materials even then only remotely related to our invention.

It needs to be emphasized that although this application will stress the utilization of the resins of our invention in the production of multilayer circuit boards, the resins may be useful in fabricating composites generally. Consequently, it needs to be explicitly recognized that the resins of our invention are intended for composite manufacture without any limitations other than those imposed by the product specifications themselves.

SUMMARY OF THE INVENTION

The purpose of our invention is to provide themosetting resins whose properties make them desirable in the preparation of composites, especially in laminated multilayer boards of a glass fiber in a polymer matrix. An embodiment comprises the vinylbenzyl ethers of the oligomeric condensation product of certain dihydric phenols and formaldehyde. In a more specific embodiment the dihydric phenol is what is commonly known as bisphenol-A. In a more specific embodiment the vinylbenzyl ether is a mixture of meta-and para-substituted vinylbenzyl ether. In a still more specific embodiment the aromatic rings are substituted with a methyl group. In still another embodiment from about 50 to 100% of the ether moieties are vinylbenzyl ether moieties, with the remainder being primary alkyl moieties containing from 1 to about 4 carbon atoms. Other embodiments will become apparent from the following description.

DESCRIPTION OF THE INVENTION

Our invention is a class of thermosetting resins of vinylbenzyl ethers of the oligomeric condensation products of a dihydric phenol and formaldehyde where from 50 to 100% of the ether groups are vinylbenzyl moieties and the remainder, if any, are alkyl moieties containing 1 to 10 carbon atoms or the benzyl moiety. Especially where all the ether moieties are the vinylbenzyl group, the extensively cross-linked polymers resulting from curing the thermosetting resins of this invention have improved properties with regard to their use in printed circuit boards. In particular, they have a dielectric constant which is better than conventional materials, a coefficient of thermal expansion which is better than conventional materials, show excellent solvent resistance (low water pickup), exhibit an improved glass transition temperature, and have a higher flow viscosity in solution at room temperature relative to conventional materials. Our thermosetting resins may be depicted by the formula,

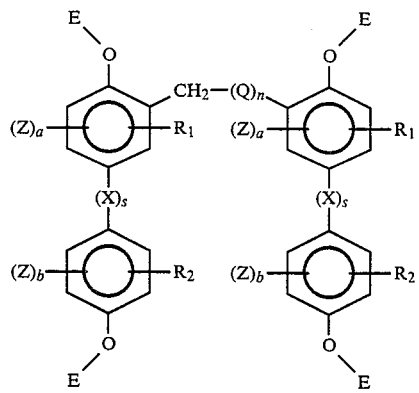

The resins of this invention result from the etherification of oligomers which are the condensation product of a dihydric phenol and formaldehyde. Therefore the product will be a mixture of materials with varying molecular weight, that is, the resulting resins are mixtures having discrete components of differing degrees of oligomerization. What needs to be emphasized is that the resins are a mixture of oligomers, and the number, n, of recurring units Q generally will vary from 0 to 10. That is, n is 0 or an integer from 1 to 10, where in the preferred practice of our invention it is 0 or an integer from 1 to 6. As previously mentioned, a spectrum of oligomers typically result from the condensation reaction, and in a desirable branch of our invention the number average of n is about 3, i.e., from 0 to about 5.

The recurring unit Q itself has the structure,

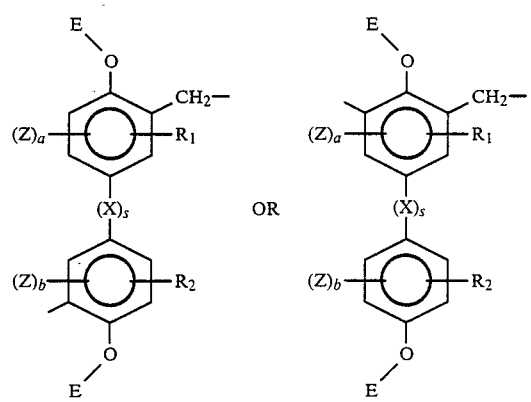

Note that the condensation may occur either on the same ring, as in the right hand structure, or in different rings, as in the left hand structure. The aromatic rings in the recurring unit Q are either joined directly or are separated by an intervening atom furnished by the moiety X. Therefore, s is 0 or 1.

Each of the moieties X may be either a methylene $[CH_2]$, isopropylidene $[C(CH_3)_2]$, hexafluoroisopropylidene $[C(CF_3)_2]$, an oxygen, sulfur, sulfonyl $[S(O)_2]$, carbonyl $[C(O)]$, or a dioxyphenylene group $[OC_6H_4O]$, where the oxygens of the latter generally are para or meta to each other. In a favored embodiment X is isopropylidene.

Each of the aromatic rings may bear substituents or may be completely unsubstituted. Thus, $R_1$ and $R_2$ are independently selected from moieties such as hydrogen, alkyl moieties containing from 1 to 10 carbon atoms, the phenyl moiety, alkoxy moieties containing from 1 to 10 carbon atoms, and phenoxy, $C_6H_5O$. Examples of suitable alkyl moieties include methyl, ethyl, propyl, butyl, pentyl, hexyl, heptyl, octyl, nonyl, and decyl moieties. The methyl and tert-butyl groups are preferred alkyl moieties in the practice of our invention, although the variant where $R_1 = R_2 = H$ is quite desirable.

The basic resins also can be readily modified to be flame retardant by incorporating halogen atoms into the aromatic rings. Thus, Z may be a halogen atom, especially bromine, and where the aromatic ring is halogenated a and b is an integer from 1 to 4. Polyhalogenated materials are desired as flame retardants, which means that a and b are recommended to be 2, 3, or 4. Where the aromatic rings are not halogen substituted then both a and b are 0.

The oligomeric condensation products have a multiplicity of phenolic hydroxyl groups substantially all of which are end-capped as ether groups in our thermosetting resins. The best case results where the ether portion, E, is a vinylbenzyl moiety, that is, of the structure.

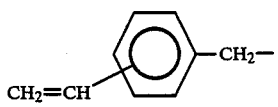

which may be either the meta-or para-isomer, and which usually is a mixture of the meta-and para-isomers. However desirable it may be to have all the phenolic hydroxyls end-capped with vinylbenzyl moieties, there is a decided cost advantage when fewer than all of the ether groups are vinylbenzyl, usually at the expense of a somewhat lower dielectric constant. In our invention it is required that at least 50% of the E moieties be a vinylbenzyl moiety, but a product with better performance characteristics results when from 70 to 100% of the ether groups are vinylbenzyl, and the best product results when 95 to 100% of such groups are vinylbenzyl.

In those cases where less than all of the ether groups are vinylbenzyl, then we are partial to resins where E is an alkyl group containing from 1 to 10 carbons or a benzyl group. Where E is an alkyl group, the primary alkyl groups are given priority, especially the primary lower alkyl groups containing from 1 to 4 carbon atoms. Thus, the most desirable alkyl groups consist of methyl, ethyl, 1-propyl, 1-butyl, and 2-methyl-1-propyl. Other alkyl groups are represented by 1-pentyl, 1-hexyl, 1-heptyl, 1-octyl, 1-nonyl, 1-decyl, 2-methyl-1-butyl, 3-methyl-1-butyl, 2,3-dimethyl-1-butyl, 3,3-dimethyl-1-butyl, 2-methyl-1-pentyl, and so forth. However, it is to be emphasized that a benzyl group also operates quite satisfactorily in the practice of our invention.

The resins of our invention may be prepared by acid catalyzed condensation of dihydric phenols with formaldehyde followed by end-capping substantially all the phenolic hydroxyls by converting them to ethers. Acid catalyzed condensation is preferred to avoid the formation of terminal hydroxy methylene groups, $—CH_2OH$. End-capping by ether formation can be effected by any suitable means, such as by reacting the phenolic condensation product with an alkyl or benzyl halide in a basic medium. The resulting thermosetting resins are readily polymerized with attendance cross-linking by a variety of curing means. In a preferred mode, curing is effected by thermal means, generally autoinitated by heating the resin in the air at a temperature between about 100° and 250° C., and more particularly between about 120° and 200° C. In practice multilayer boards may be laminated at a temperature between about 150° and about 200° C. for 0.5–5 hours with postcuring at about 180°–250° C. for about 0.5-24 hours. Curing also may be brought about by chemical means using a free radical initiator such as azo-bis-isobutyronitrile, benzoyl peroxide, di-t-butyl peroxide, etc. Curing may be effected as well by irradiation, especially by visible and ultraviolet light in the presence of a suitable photoinitiator. Whether thermal, chemical, or photochemical curing is performed, the resin becomes extensively cross-linked and sets to an infusible, insoluble glassy solid.

The materials of our invention also can be blended with other types of vinylbenzyl ethers of functionality greater than or equal to 2 to provide A-stage varnish solutions with tailorable viscosity and variable properties in the cured product such as glass transition temperature, heat distortion temperature, fracture toughness, etc. For example, our resins could be blended with various styrenated bisphenols to raise cross-link density and improve processability of the bis-styryl compound. The materials of our invention are polymers of moderate functionality (i.e., number of vinylbenzyl groups per molecule) and viscosity and they can be incorporated to reduce crystallinity of various styrenated bisphenols where the bisphenols are exemplified by the formula

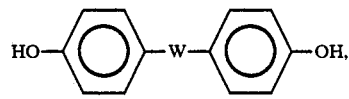

with W being $—O—$, $—C(CH_3)_2—$, $—SO_2—$, $—CO—$, and so forth to raise the resin solids content in the A-stage varnish solution, to raise the resin content in the B-stage, and to reduce the amount of resin flow in the C-stage. High-to-moderate molecular weight poly(vinylbenzyl ethers) also may be useful for improving the shelf life of other styrenated oligomers, and may raise the ductility of the otherwise brittle laminate, such as in the case of styrenated bisphenol A.

The following examples are merely illustrative of our invention and are not limiting in any way.

EXAMPLE 1

Preparation of Styrene Terminated Bisphenol-A-Formaldehyde (STBPA-F). Bisphenol-A-formaldehyde resin was prepared as follows. 150.0 g (0.658 moles) of bisphenol-A was dissolved in 500 ml of ethanol in a 1 liter round bottom flask equipped with condenser and magnetic stirrer. To this reaction mixture was added 0.5 ml of concentrated sulfuric acid. The solution was heated to reflux and then 14.5 g (0.151 moles) of paraformaldehyde was added gradually to the reaction. The reaction was heated at reflux with stirring for 48 hours and then allowed to cool to room temperature. The reaction was neutralized with aqueous sodium hydroxide solution and then concentrated under vacuum, yielding 130.3 g of viscous syrup, with a $M_w = 362$.

50.0 g (0.1062 moles) of bisphenol-A formaldehyde resin and 71.35 g (0.4675 moles) of vinylbenzyl chloride (60/40 meta/para isomer ratio) were dissolved in 110 ml of acetone in a three neck-round bottom flask equipped with condenser, addition funnel, thermometer, mechanical stirrer and nitrogen purge. The reaction mixture was heated at reflux (65°–70° C. temperature) for a period of one hour, following which a solution of 41.83 g (0.746 moles) of potassium hydroxide in 93 ml of methanol was added to the warm reaction mixture over an interval of one hour. The reaction was stirred thereafter at ambient temperature for a period of 24 hours. The reaction mixture was recovered, dried over magnesium sulfate, filtered, and concentrated under vacuum. The resulting oil was dried in a vacuum oven at ambient temperature overnight and yielded 24.5 g of resin.

EXAMPLE 2

Preparation of Cured STBPA-F. 3.3 g of STBPA-F of Example 1 was placed in a flat casting dish and cured by heating in an oven at a temperature of 120° C. for a period of 2 hours, followed by a 16 hour cure at 160° C. and a 2 hour cure at 200° C. Following this, the sample was then post-cured for a period of 2 hours at 225° C. and recovered. The cured polymer was found to have a glass transition temperature (Tg) of greater than 300° C., a minor softening point (Tsp) (measured via Thermal Mechanical Analysis (TMA)) at 165±5° C., a coefficient of thermal expansion from 25° to 165° C. of 40±2 ppm/°C. and from 25° to 260° C. of 65±3 ppm/°C. The dielectric constant at 1 MHz and dissipation factor at 0% and 50% relative humidity are summarized in the following table.

TABLE 1

| Relative Humidity | Dielectric Constant | Dissipation Factor |
| --- | --- | --- |
| 0% | 2.94 ± 0.27 | 0.004 ± 0.001 |
| 50% | 3.25 ± 0.17 | 0.013 ± 0.001 |

EXAMPLE 3

Preparation of Cured STBPA-F from Chloroform Solution. 2.0 g of STBPA-F resin of Example 1 was dissolved in about 10 milliliters of chloroform. The resulting solution was transferred to a flat casting dish and heated on a hot plate to remove a major portion of the chloroform solvent. The sample was then cured in an oven at 120° C. for 2 hours, followed by 16 hours at 160° C. and 2 hours at 200° C. The sample was post cured at 225° C. for 1 hour. The cured polymer was found to have the following properties: glass transition temperature (Tg)>300° C., coefficient of thermal expansion from 25 to 260° C. ($\alpha_{260}$) of 59±4 ppm/°C. and a dielectric constant and dissipation factor (1 MHz) at 0% relative humidity of 2.63±0.17 and 0.007±0.001, respectively.

EXAMPLE 4

Preparation of Styrene Terminated Polybrominated Bisphenol-A Formaldehyde (STBBPA-F). 40.57 (0.086 moles) of bisphenol-A formaldehyde resin, 40 milliliters of carbon tetrachloride, 84 milliliters of methanol and 1.99 g of potassium bromide were charged into 500 ml three neck-round bottom flask equipped with condenser, addition funnel, nitrogen purge and magnetic stirring bar. The reaction vessel was placed in a water bath and heated to a temperature of about 50° C. To this 2-phase reaction mixture was added 41.25 milliliters (0.800 moles) of bromine dropwise over a 4 hour period. At the end of this time 80 milliliters of water was added to the reaction mixture and a distillation head attached to the reaction vessel, and the volatile products were distilled off at atmospheric pressure. The remaining residue was taken up in 160 milliliters of dichloromethane and the organic phase was washed three times with 80 milliliters of water and then twice with 80 milliliters of 10% aqueous sodium bisulfite to remove any residual bromine which may be present. The organic phase was washed with 80 milliliters of water and dried over sodium sulfate. The methylene chloride was removed under vacuum and then azeotropic drying with ethanol gave 80.70 grams of product.

40.0 g (0.425 moles) of the above polybrominated bisphenol-A formaldehyde resin and 28.54 g (0.187 moles) of vinylbenzyl chloride (60/40 meta/para isomer ratio) were dissolved in 90 ml of acetone in a three neck-round bottom flask equipped with condenser, addition funnel, thermometers, mechanical stirrer and nitrogen purge. The reaction mixture was heated to reflux (65°–70° C. temperature) for a period of one hour, following which a solution of 12.54 g (0.224 moles) of potassium hydroxide in 28 milliliters of methanol was added to the warm reaction mixture over a period of one hour. Thereafter the reaction was stirred at ambient temperature for a period of 24 hours. The reaction mixture was recovered, dried over magnesium sulfate, filtered and concentrated under vacuum. The resulting oil was dried in a vacuum oven at ambient temperature overnight and yielded 30.8 g of resin.

EXAMPLE 5

Preparation of Cured STBBPA-F. 5.0 g of STBBPA-F resin of Example 4 was placed in a flat casting dish and cured by heating in an oven at a temperature of 120° C. for 2 hours, followed by a 16 hour cure at 160° C. and a 2 hour cure at 200° C. The sample was post-cured for a period of 2 hours at 225° C. and recovered. The cured polymer was found to have the followed properties: glass transition temperature (Tg)>250° C., and dielectric constant (1 MHz) and dissipation factor at 0 and 50% relative humidity as tabulated in Table 2.

TABLE 2

| Relative Humidity | Dielectric Constant | Dissipation Factor |
| --- | --- | --- |
| 0% | 3.01 ± 0.16 | 0.002 ± 0.001 |
| 50% | 2.98 ± 0.02 | 0.009 ± 0.001 |

EXAMPLE 6

Preparation of Cured STBBPA-F from Chloroform Solution. 2.0 g of STBBPA-F resin of Example 4 was dissolved in 10 milliliters of chloroform. The resulting solution was transferred to a flat casting dish and heated on a hot plate to remove the majority of the solvent, the sample was then cured in an oven at 120° C. for 2 hours, followed by 16 hours at 160° C. and 2 hours at 200° C. The sample was post-cured at 225° C. for 1 hour. The cured polymer was found to have the following properties: glass transition temperature (Tg)>250° C., and dielectric constant and dissipation factor at 0% and 50% relative humidity as tabulated in Table 3.

TABLE 3

| Relative Humidity | Dielectric Constant | Dissipation Factor |
| --- | --- | --- |
| 0 | 2.82 ± 0.16 | 0.004 ± 0.002 |
| 50 | 2.77 ± 0.008 | 0.012 ± 0.001 |

EXAMPLE 7

Preparation of Cured STBPA; Comparison of Selected Properties. Styrene terminated bisphenol-A was prepared according to the method of Steiner (U.S. Pat. No. 4,116,936) by reacting vinylbenzyl chloride with bisphenol-A. This resin was cured by taking 2.0 g of STBPA and was dissolved in about 10 milliliters of chloroform in a flat casting dish and heated on a hot plate to remove the majority of the solvent. The sample was then cured in an oven at 120° C. for 2 hours, followed by 16 hours at 160° C. and 2 hours at 200° C. The sample was postcured for 1.5 hours at 225° C. The cured polymer had the following properties: glass transition temperature (Tg)>250° C., minor softening point (Tsp) (measured via TMA) at 168±11° C., a coefficient of thermal expansion from 25° to 168° C. of 57±8 ppm/°C. and from 25° to 260° C. of 71±23 ppm/° C. The dielectric constant at 1 MHz and dissipation factor at 0% and 50% relative humidity are summarized in the following table.

TABLE 4

| Relative Humidity | Dielectric Constant | Dissipation Factor |
|---|---|---|
| 0 | 2.93 ± 0.11 | 0.003 ± 0.002 |
| 50 | 3.15 ± 0.14 | 0.013 ± 0.001 |

What is claimed is:

1. The polymeric product resulting from curing a resin which is a vinylbenzyl ether of the oligomeric condensation product of a dihydric phenol and formaldehyde and with the formula:

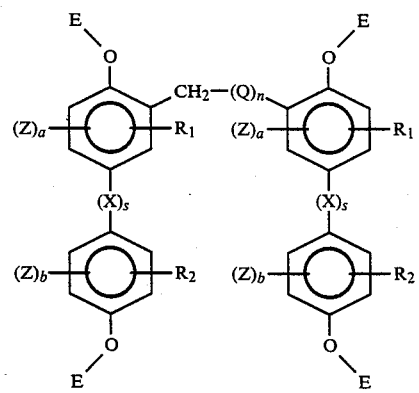

where the recurring unit Q has the structure,

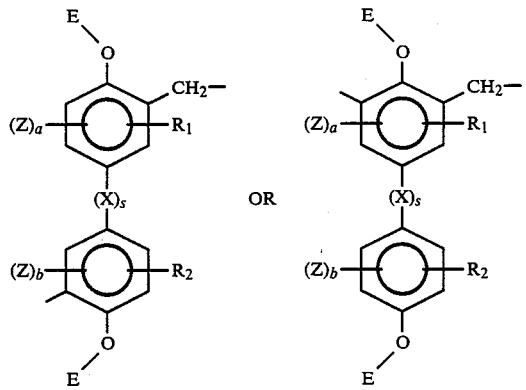

and n is an integer from 1 to 10;
s is 0 or 1;
each X is independently selected from the group consisting of $CH_2$, $C(CH_3)_2$, $C(CF_3)_2$, $S(O)_2$, $C(O)$, and $OC_6H_4O$;
each $R_1$ and $R_2$ is independently selected from the group consisting of hydrogen, alkyl and alkoxy moieties containing 1 to 10 carbon atoms, phenyl, and phenoxy;
a and b are independently 0 or integers from 1 to 4;
Z is Cl or Br;
E is selected from the group consisting of vinylbenzyl moiety, alkyl moieties containing 1 to 10 carbon atoms, or benzyl, subject to the constraint that at least 50% of all E's are the vinylbenzyl moiety.

2. The polymeric product of claim 1 where each $R_1$ and $R_2$ is selected from the group consisting of hydrogen, methyl, and tert-butyl moieties.

3. The polymeric product of claim 2 where all $R_1$ and $R_2$ are hydrogen.

4. The polymeric product of claim 2 where all $R_1$ and $R_2$ are methyl.

5. The polymeric product of claim 1 where s is 1 and X is $C(CH_3)_2$.

6. The polymeric product of claim 1 where Z is Br and each of a and b is an integer from 1 to 4.

7. The polymeric product of claim 1 where E is a primary alkyl moiety containing from 1 to 10 carbon atoms.

8. The polymeric product of claim 7 where the alkyl moiety contains 1 to 4 carbon atoms.

9. The polymeric product of claim 1 where E is benzyl.

10. The polymeric product of claim 1 where from 70 to 100% of the E moieties are the vinylbenzyl moiety.

11. The polymeric product of claim 10 where from 95 to 100% of the E moieties are vinylbenzyl moieties.

12. The polymeric product of claim 1 where n is an integer from 1 to 6.

13. The polymeric product of claim 2 where the number average of n is about 3.

14. The polymeric product of claim 1 where curing is effected by heating at a temperature from about 100° C. to about 250° C.

15. The polymeric product of claim 14 where the temperature is from about 120° to about 200° C.

16. The polymeric product of claim 1 where curing is effected with the aid of a free radical initiator.

17. The polymeric product of claim 1 where curing is effected by irradiation.

* * * * *